United States Patent [19]

Jablonski et al.

[11] 4,122,076

[45] Oct. 24, 1978

[54] PROCESS OF PREPARING MALEIMIDES

[75] Inventors: Richard J. Jablonski, Scotia; Daniel Kruh, Schenectady, both of N.Y.

[73] Assignee: General Electric Company, Schenectady, N.Y.

[21] Appl. No.: 93,436

[22] Filed: Nov. 27, 1970

[51] Int. Cl.$^2$ ............................................. C08G 73/12
[52] U.S. Cl. .............................. 528/322; 260/326.26; 260/326.5 FM
[58] Field of Search .......... 260/78 TF, 78 UA, 326.5, 260/326.26 FM

[56] References Cited

U.S. PATENT DOCUMENTS

| | | | |
|---|---|---|---|
| 2,524,136 | 10/1950 | Prill | 260/326.5 FM |
| 2,524,145 | 10/1950 | Tawney | 260/326.5 FM |
| 3,485,796 | 12/1969 | Naselow | 260/47 |
| 3,562,223 | 2/1971 | Bargain et al. | 260/78 |
| 3,652,511 | 3/1972 | Vincent et al. | 260/78 |
| 3,868,348 | 2/1975 | Berlin et al. | 260/78 TF |

*Primary Examiner*—Howard E. Schain

[57] ABSTRACT

Imide group containing solutions are prepared by reacting the Diels-Alder reaction product of furan and maleic anhydride with amine, heating the resultant amic acid to form the maleimide material with regeneration of furan. The imide-containing products can be isolated.

8 Claims, No Drawings

PROCESS OF PREPARING MALEIMIDES

This invention relates to new and improved means for producing maleimides. More particularly, it relates to such means which provide for the preparation of the maleimide group-containing material in solution with ready regeneration of part of the starting materials.

Generally speaking, in the preparation of maleimides from the corresponding maleamic acids, dehydrating agents such as acetic anhydride and sodium acetate are used as set forth in U.S. Pat. Nos. 2,444,536; 3,127,414 and British Pat. No. 1,137,592. Alternatively, acetic anhydride or ketene and a trialkyl amine are used in U.S. Pat. No. 3,013,290. To free the imide from such reactants and solvents for bulk use, one must precipitate the maleimide and thoroughly wash and dry the material prior to further use. The resulting by-products such as acetic acid must be recycled to the anhydride as by using a ketene generator. The corrosive nature of the dehydrating agents or by-products, or both, makes necessary the use of corrosion-resistant reactors such as of glass, and the precipitation, washing and drying which are necessary substantially increase labor and equipment costs.

From the above it will be quite apparent that it is desirable to prepare maleimide materials in situ in solution by an economical process without the handling of corrosive materials, and it is a primary object of this invention to provide such a process in which the use of dehydrating materials and recycling and precipitation problems are eliminated. Those features of the invention which are believed to be novel are set forth with particularity in the claims appended hereto. The invention will, however, be understood and further objects and advantages thereof appreciated from a consideration of the following description.

Briefly, according to the present invention, amine is reacted with the Diels-Alder reaction product of furan and maleic anhydride to produce amic acid material which is then heated to produce the corresponding imide. Further heating of the imide material results in the splitting off of furan, leaving the imide of the particular amine precursor. This imide in solution can be reacted with more amine.

The Diels-Alder reaction product of maleic anhydride and furan, specifically 7-oxabicyclo [2.2.1]hept-5-ene-2,3-dicarboxylic anhydride, is well known and is simply prepared by reacting together furan and maleic anhydride. Any amine can be used, it only being necessary that it contain at least one amino group which can react with the Diels-Alder anhydride. The amine which can be used in excess or in equivalent amount can be aliphatic, substituted or unsubstituted aliphatic, aromatic, aralkyl, alkaryl, heterocyclic and the like, mixtures of various amines being also useful, as well as ammonia, urea and others which contain at least one amine group.

Among the polyamines useful in connection with the present invention are those expressed by the formula $$X-R-(NH_2)_n$$

where R is an organic radical and $n$ is at least 2, and X is hydrogen, an amino group or organic group including those also containing at least one amino group. Among the specific amines useful for the present invention, alone or in admixture, are the following:

4,4-diamino-2,2'-sulfonediphenylmethane
ethylenediamine
benzoguanamine
meta-phenylene diamine
para-phenylene diamine
4,4'-diamino-diphenyl propane
4,4'-diamino-diphenyl methane
benzidine
4,4'-diamino-diphenyl sulfide
4,4'-diamino-diphenyl sulfone
3,3'-diamino-diphenyl sulfone
4,4'-diamino-diphenyl ether
2,6-diamino-pyridine
bis(4-amino-phenyl)diethyl silane
bis(4-amino-phenyl)diphenyl silane
bis(4-amino-phenyl)phosphine oxide
4,4'-diaminobenzophenone
bis(4-amino-phenyl)-N-methylamine
bis(4-aminobutyl)tetramethyldisiloxane
1,5-diaminonaphthalene
3,3'-dimethyl-4,4'-diamino-biphenyl
3,3'-dimethoxy benzidine
2,4-bis(beta-amino-t-butyl)toluene
toluene diamine
bis(para-beta-amino-t-butyl-phenyl)ether
para-bis(2-methyl-4-amino-pentyl)benzene
para-bis(1,1-dimethyl-5-amino-pentyl)benzene
m-xylylene diamine
p-xylylene diamine
bis(4-amino-cyclohexyl)methane
hexamethylene diamine
heptamethylene diamine
octamethylene diamine
nonamethylene diamine
decamethylene diamine
3-methyl-heptamethylene diamine
4,4'-dimethylheptamethylene diamine
2,11-diamino-dodecane
1,2-bis-(3-amino-propoxy)ethane
2,2-dimethyl propylene diamine
3-methoxy-hexamethylene diamine
2,5-dimethylhexamethylene diamine
2,5-dimethylheptamethylene diamine
5-methylnonamethylene diamine
1,4-diamino-cyclo-hexane
1,12-diamino-octadecane
2,5-diamino-1,3,4-oxadiazole
$H_2N(CH_2)_3O(CH_2)_2O(CH_2)_3NH_2$
$H_2N(CH_2)_3S(CH_2)_3NH_2$
$H_2N(CH_2)_3N(CH_3)(CH_2)_3NH$
polymethylene polyamine (Curithane)
and mixtures thereof.

The following examples will illustrate the practice of the present invention, it being realized that they are to be taken as exemplary only and not limiting in any way.

EXAMPLE 1

The Diels-Alder reaction product of furan and maleic acid anhydride, specifically 7-oxabicyclo [2.2.1] hept-5-ene-2,3-dicarboxylic anhydride, and aniline were mixed together without solvent in the amount of 0.10 mole each. An initial exotherm was observed accompanied by partial solubility. There was then added to the mixture 45 cc of N-methylpyrrolidone (MP), resulting in nearly complete initial solubility. However, within about ten minutes a slush was formed, the mixture being then heated to about 80° C over a period of about 20 minutes to effect dissolution. About 5 cc of the reaction mixture was precipitated in water, washed with water and washed in hexane and then dried. The nuclear magnetic resonance spectrum of the white resulting solid showed it to be amic acid corresponding to the combination of the original reactants. The remainder of the reaction mixture was heated to about 145° C over a period of about 40 minutes and the temperature then increased to 165° C over a period of 1 hour and this temperature maintained for an additional hour. The distillate was identified by NMR spectroscopy to be furan and water. The reaction mixture was then allowed to cool to room temperature and further analysis by NMR spectroscopy showed the presence of N-phenyl-maleimide. Precipitation of the reaction mixture in water produced a solid which was collected by filtration. Recrystallization of this solid from a 10:1 volumetric mixture of acetone in water produced yellow crystals melting over the range of 89°–90° C.

EXAMPLE 2

Into a flask equipped with stirrer, thermometer and distillation apparatus there were placed 33.2 g (0.10 mole) of 7-oxabicyclo [2.2.1]hept-5-ene-2,3-dicarboxylic anhydride and 100 cc of MP solvent. An equivalent amount of methylene dianiline was added along with a further amount of 75 cc of MP solvent, complete dissolution occurring within about 10 minutes. The mixture was stirred for 1½ hours and then heated to 145° C to 175° C for 3¼ hours while furan and water were collected by distillation. The mixture was allowed to cool to room temperature. Analysis of the NMR spectroscopy showed the formation of the bismaleimide of methylene dianiline. The product was isolated by precipitation into water.

The imide group containing solution is readily reacted with further amine which is either present in the original solution or added separately.

EXAMPLE 3

Into a flask equipped with thermometer, stirrer and fitted with a distillation apparatus there were placed 36.5 g (0.22 mole) of 7-oxa-bicyclo [2.2.1]hept-5-ene-2,3-dicarboxylic anhydride and 18.6 g (0.20 mole) of aniline at room temperature. Within 5 minutes the reaction exotherm raised the temperature to 55° C, at which point there were added 40 cc of dimethylacetamide (DMAC), the resultant slurry being mixed for 15 minutes. The reaction temperature was increased to 90° C over a period of about ½ hour, at which time distillation of furan began. The reaction temperature was then increased to 135° C to 145° C over a period of about ½ hour and maintained at this temperature for about 45 minutes while the theoretical amount of furan was collected by distillation. The mixture was then cooled and precipitated into 100 cc of ice water, the precipitate being collected by filtration and recrystallized from a benzene/acetone mixture. The resultant product in the amount of 25.5 g had a melting point over the range of 87°–88° C which is that of N-phenylmaleimide.

EXAMPLE 4

A solution of 297 g (1.5 moles) methylene dianiline in 207.5 g of MP solvent containing xylene was treated at 180° C with stirring and under a blanket of nitrogen with 230.4 g (1.2 moles) of trimellitic anhydride added portionwise. Heating was continued for 21 hours at 150° C to 210° C using 1.5 g of triethylphosphite as a catalyst. Titration of the residual carboxyl showed the reaction to be essentially complete. The product was diluted to 25% solids to give 1924 g of amine solution. 242 g (containing 0.08 mole of amine) of this solution was treated at 40° C with 13.8 g of (0.08 mole) 7-oxa-bicyclo [2.2.1]hept-5-ene-2,3-dicarboxylic anhydride, stirred for 75 minutes and let stand for about 60 hours at room temperature. Titration gave a carboxyl content of 5.0% as against a theoretical 5.4%. Using equipment modified for distillation, 0.0095 g of hydroquinone was added and the solution heated to 170° C and held for one hour while vacuum was applied. The distillate analyzed by NMR spectroscopy was shown to contain 4.9 g of furan as against a theoretical 5.6 g and 1.5 g of water as against the same theoretical amount. A film was cast from this solution and cured 15 minutes each at 180° C and 230° C and 1 hour at 316° C. The resulting cured film was flexible and crease-resistant. When aged at 250° C in a forced air oven, the film lost 11% of its weight in 712 hours. A portion of the solution was precipitated into water with vigorous stirring, filtered, washed, and dried. The infrared spectrum of the resulting powder showed the presence of maleimide group.

The following shows that the present process produces a product identical to that of a prior art process. A 472 g portion of the above solution (containing 0.15 mole of the above amine) was treated with 15.7 g (0.16 mole) of maleic anhydride at 40° C, stirred for 1.5 hours and let stand at room temperature for about 16 hours. Carboxyl titration gave 5.3% as against a theoretical 5.0%. Then 32.6 g (0.33 mole) of acetic anhydride and 1.8 g (0.02 mole) of sodium acetate were added and the solution heated to 55° C under nitrogen with stirring for 2 hours. The reactant mixture was cooled to room temperature and allowed to stand for about 16 hours. The product was then precipitated into water with vigorous stirring, filtered, washed and dried. The infrared spectrum of the resulting powder showed the presence of the maleimide group. A 25% solids solutions of this powder in MP solvent was prepared and a film cast therefrom which was cured for 15 minutes each at 180° C, 230° C, and one hour at 316° C. The film at this stage was flexible and crease resistant. When aged for 712 hours at 250° C, a weight loss of 11% was recorded.

There is provided, then, by this invention a convenient and economical process for preparing maleimide group-containing material from the reaction of the reaction product of furan and maleic anhydride with amine.

What we claim as new and desire to secure by Letters Patent of the United States is:

1. The process of preparing a maleimide which consists essentially of reacting the Diels-Alder reaction product of furan and maleic anhydride with amine using a solvent reaction medium and heating the resultant amic acid to produce the maleimide of the amine and furan, said process taking place entirely in the reaction medium.

2. A process as in claim 1 where said amine is methylene dianiline.

3. A process as in claim 1 where said amine is aniline.

4. A process as in claim 1 wherein said amine is ammonia.

5. A process as in claim 1 wherein said amine is urea.

6. A process as in claim 1 wherein said amine is the reaction product of a tricarboxylic acid anhydride and diamine.

7. A process as in claim 6 in which said tricarboxylic acid anhydride is trimellitic anhydride and said diamine is methylene dianiline.

8. The process of claim 1 wherein said imide still in solution is reacted with further amine.

* * * * *